United States Patent [19]
Saari et al.

[11] 4,160,712
[45] Jul. 10, 1979

[54] PROCESS FOR PREPARING NOVEL N-CARBOXYL-α-AMINO ACID ANHYDRIDES

[75] Inventors: Walfred S. Saari; Joel R. Huff, both of Lansdale, Pa.

[73] Assignee: Merck & Co., Inc., Rahway, N.J.

[21] Appl. No.: 895,846

[22] Filed: Apr. 13, 1978

Related U.S. Application Data

[62] Division of Ser. No. 773,258, Mar. 1, 1977, Pat. No. 4,120,971.

[51] Int. Cl.$^2$ .................. B01J 1/10; C07D 263/02
[52] U.S. Cl. ...................... 204/158 R; 260/307 B
[58] Field of Search ........................ 204/158 R

[56] References Cited

U.S. PATENT DOCUMENTS 3,956,367  5/1976  Kollonitsch .................. 204/158 R

*Primary Examiner*—Howard S. Williams
*Attorney, Agent, or Firm*—Daniel T. Szura; Harry E. Westlake, Jr.

[57] ABSTRACT

N-carboxyanhydrides of hydroxyphenylalanines are disclosed. The compounds have antihypertensive activity.

8 Claims, No Drawings

PROCESS FOR PREPARING NOVEL N-CARBOXYL-α-AMINO ACID ANHYDRIDES

BACKGROUND OF THE INVENTION

This is a division of application Ser. No. 773,258, filed, Mar. 1, 1977 which issued Oct. 17, 1978, as U.S. Pat. No. 4,120,971.

The present invention is concerned with N-carboxyanhydrides of hydroxyphenylalanines and their use as antihypertensives.

L-3-(3,4-Dihydroxyphenyl)-2-methylalanine is a known antihypertensive agent (U.S. Pat. No. 3,344,023). α-Methyltyrosine is known to be useful for treating hypertension caused by pheochromocytoma. N-Carboxyanhydrides of various amino acids, including tyrosine and phenylalanine, are also known. (See "Synthetic Polypeptides". C. H. Bamford et al, p 53–58, Academic Press, New York, N.Y., 1956).

The N-carboxyanhydrides of 3-(3,4-dihydroxyphenyl)-2-methylalanine and α-methyltyrosine are novel compounds having pharmaceutical activity.

SUMMARY OF THE INVENTION

N-carboxy anhydrides of L-3-(3,4-dihydroxyphenyl)-2-methylalanine and L- α-methyltyronsine and use as antihypertensive agents.

DESCRIPTION OF THE PREFERRED EMBODIMENTS

An embodiment of this invention is compounds having the formula

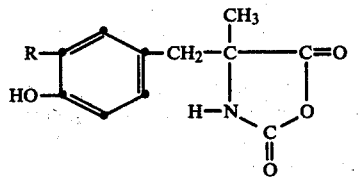

I wherein R is hydrogen or hydroxy.

Compounds of Formula I contain an asymmetric carbon atom and are optically active. The individual optical isomers may be variously designated as L and D, l and d, or − and +. The designations S (sinister) and R (rectus) indicate the absolute spatial configurations of the isomers and may also be used to identify the individual optical isomers. When no particular optical isomer is designated, the compound or formula includes the individual optical isomers, racemate (e.g. D,L or R,S) and mixtures of optical isomers. The S-isomer of Formula I compounds is preferred.

A more preferred compound has the formula

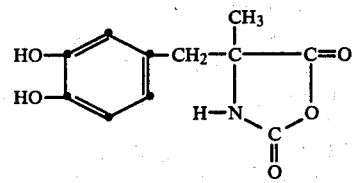

II

The S-isomer of II is most preferred.

Another preferred compound has the formula

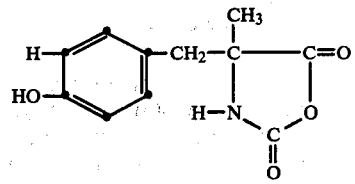

III

The S-isomer of III is more preferred.

The S-isomer of compound II was tested in vivo in spontaneously hypertensive (SH) rats and found to have antihypertensive (blood pressure lowering) activity. This data indicate that the compound of Formula I are useful for treating hypertension (high blood Pressure) in human patients.

The present compounds may be administered to hypertensive patients, orally or parenterally i.e. intravenously, intraperitoneally, intramuscularly etc., in a suitable dosage form e.g. tablet, capsule, sterile solution, elixir and the like. The daily dosage is varied and may range from 10 mg to 3.5 grams, preferably from 10 mg to 2500 mg, more preferably from 100 mg to 2000 mg and most preferably from 250 to 1500 mg. The dosage forms are prepared using conventional procedures and compounding ingredients, as necessary.

The compounds of the present invention are synthesized by conventional procedures. One such procedure involves preparing the N-carboxyanhydride in which the phenolic hydroxyl groups are protected with a blocking group, and then deblocking by hydrogenation in a non-aqueous system. A useful preparation procedure is illustrated by the following reaction equations:

Step 1

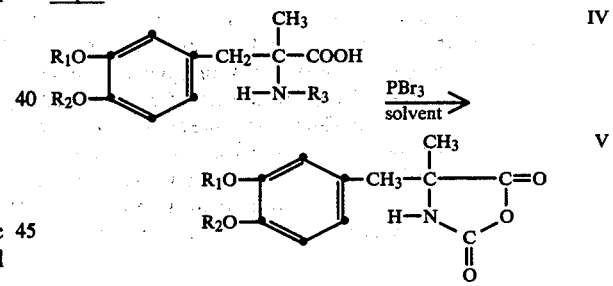

Step 2

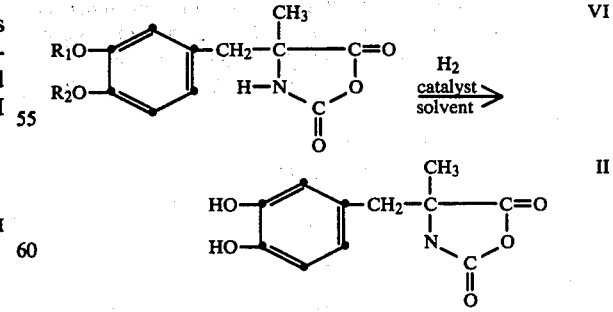

$R_1$ and $R_2$ are phenolic blocking or protecting groups which are selectively removed by catalytic hydrogenation in a non-aqueous system. Examples of especially suitable blocking groups are the carboalkoxy groups having the formula

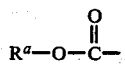

where $R^a$ is benzyl or substituted benzyl e.g. p-methoxybenzyl, p-nitrobenzyl, p-bromobenzyl and the like. The $R_1$ and $R_2$ groups may also be joined to form a ketal

where $R_4$ is H, $C_1$-$C_5$ alkyl, benzyl or aryl (e.g. phenyl, tolyl etc.) and $R_5$ is aryl or substituted aryl, e.g. phenyl, tolyl etc.

$R_3$ is any suitable amino blocking or protecting group. Especially suitable amino blocking groups are exemplified by the carboalkoxy groups described above and carbo-t-butoxy.

The PBr$_3$ reactant in Step 1 may be replaced by PCl$_3$, PBr$_5$, PCl$_5$, POCL$_3$, POBr$_3$, P$_2$O$_5$ and the like. The solvent in this step is an aprotic solvent such as ethylether, ethylacetate, chloroform, dimethoxyethane and the like. Water must be excluded in this step.

In Step 2, a strong acid is optionally used. Examples of useful acids are strong organic acids such as trifluoroacetic, p-toluenesulfonic, methanesulfonic and the like — as well as mineral acids e.g. HCl, HBr. The acid is not essential in Step 2 but improves the rate of hydroxy blocking group removal when the blocking group is the aforesaid ketal, especially the diphenylmethylene moiety. Step 2 is also carried out in the absence of water, preferably in an aprotic solvent such as ethylether, dimethoxyethane and the like.

Hydrogenation catalysts which are useful are the noble metals, either alone or on a suitable carrier such as carbon (C), kieselguhr, silica etc. Examples of useful catalysts are Pd/C, Pt, PtO$_2$ and the like. Conventional reaction temperatures and pressures are used.

In another procedure for synthesizing the present compounds, the protected N-carboxyanhydride is prepared as in Step 1, wherein $R_1$ and $R_2$ are formyl,

The phenolic hydroxyl groups are then deblocked in a nonaqueous aprotic solvent by irradiation with light (photolysis) whose wavelength is less than 400 mm. This procedure is illustrated by the following reaction equation.

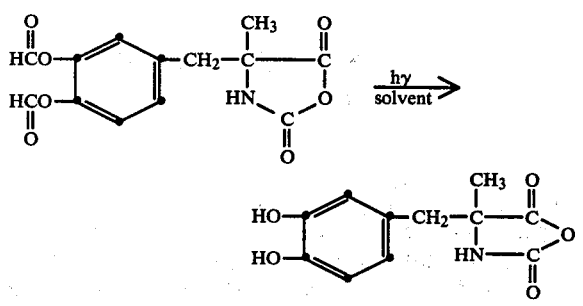

The following Examples illustrate preparation of N-carboxyanhydrides of Formula I. These compounds are derivatives of 2,5-oxazolidinedione although they are commonly referred to as N-carboxyanhydrides. All temperatures are in °C., unless otherwise indicated.

EXAMPLE 1

Step I Preparation of (S)-4-Methyl-4-(3,4-diphenylmethylenedioxybenzyl)-2,5-oxazolidinedione Phosphorous tribromide (10.2g, 37.5 mmol) in dry ethylether (100 ml) is added over a period of 1.5 hr. to a solution of (S)-N-carbobenzyloxy-3-(3,4-diphenylmethylenedioxyphenyl)-2-methylalanine (12.0g, 23.5 mmol) in dry ethylether (100 ml) under nitrogen at 25°. After addition is complete, stirring is continued for an additional 3 hr. at 20°-25°. The product begins to crystallize from the reaction medium. Dilution with dry petroleum ether (40°-60°), 1200 ml, completes the crystallization. After filtration, the crude product is washed throughly with petroleum ether to remove excess phosphorus tribromide. Recrystallization from methylene chloride — petroleum ether yields, after drying 8.1 g (86%) of (S)-4-methyl-4-(3,4-diphenylmethylenedioxybenzyl)-2,5-oxazolidinedione.

Step 2 Preparation of (S)-4-methyl-4-(3,4-dihydroxybenzyl)-2,5-oxazolidinedione (Formula II)

A solution of (S)-5-methyl-5-(3,4-diphenylmethyl enedioxybenzyl-2,4-oxazolidinedione (2.0g, 5.0 mmol) in ethyl acetate-trifluoroacetic acid (1:1v/v, 50 ml) is hydrogenated at 20°-25° and 40 psi for 24 hours, using 10% Pd/C (0.5g) as catalyst. The reaction is filtered through diatomaceous earth under nitrogen to remove the catalyst and then concentrated under vacuum (< 30°) to a volume of about 3 ml. This mixture is chromatographed over silica gel (20g), eluting with dry ethyl acetate. The fraction containing the product is concentrated under vacuum (<30°) to about 5 ml. Dilution with hexane (250 ml) causes the product to precipitate. It is filtered, washed with hexane, and dried (25°/0.1 torr) to yield 0.9 g (76%) of the (S)-4-methyl-4-(3,4-dihydroxybenzyl)-2,5-oxazolidinedione. When the racemate, (R,S)-N-carbobenzyloxy-3-(3,4-diphenylmethylenedioxyphenyl)-2-methylalanine, is used in place of the (S) isomer in Step 1, of Example 1, the corresponding racemic N-carboxyanhydride is obtained.

The N-carboxy anhydride of α-methyltyrosine [(S)- or (R,S)4-methyl-4-(4-hydroxybenzyl)-2,5-oxazolidinedione (Formula III] is obtained using substantially the same procedure as in Example 1 but substituting an appropriate amino and phenolic hydroxyl blocked α-methyltyrosine for the (S)-N-carbobenzyloxy-3-(3,4-diphenylmethylenedioxyphenyl)-2-methylalanine.

EXAMPLE 2

Step 1 Preparation of (S)-N-Carbobenzyloxy-3-(3,4-diformyloxyphenyl)-2-methylalanine (A)

A solution of (S)-N-carbobenzyloxy-3-(3,4-dihydroxyphenyl)-2-methylalanine (0.35 g, 1 mmol) and acetic formic anhydride (0.36 g, 4 mmol) in anhydrous tetrahydrofuran (5 ml) is stirred 24 hours at 20°-25° under dry N$_2$. The solvent is evaporated in vacuo and the residue is dried further at 0.1mm/25° for 2 hours. The product (A) (0.4g, 100%) is obtained as an oil.

Step 2 Preparation of (S)-4-Methyl-4-(3,4-diformyloxybenzyl)-2,5-oxazolidinedione (B)

Phosphorous tribromide (0.81g, 3 mmol) in dry ethylether (5 ml) is added dropwise to a solution of (S)-N-carbobenzyloxy-3-(3,4-diformyloxyphenyl)-2-methylalanine (0.4g, 1 mmol) in dry ethylether (10 ml). After stirring 3 hours at 20°–25° under dry nitrogen, the reaction mixture is diluted with dry petroleum ether (40°–60°) (100 ml) and refrigerated 18 hours. The solvent is decanted from the gum which has separated. The gum is dissolved in methylene chloride (2 ml) and precipitated with ethyl ether as a gum. The product (B) is separated and dried 0.1mm/25° for 3 hours over phosphorous pentoxide to afford 0.24g (80%) of gummy solid.

Step 3 Preparation of (S)-4-Methyl-4-(3,4-dihydroxybenzyl)-2,5-oxazolidinedione (C)

A solution of (S)-4-methyl-4-(3,4-diformyloxybenzyl)-2,4-oxazolidinedione (0.24g, 0.8 mmol) in dry acetonitrile (20 ml) is irradiated (Hanovia medium pressure mercury vapor lamp) with no filter for 18 hours under nitrogen. The light yellow solution is evaporated to an oil which is dissolved in ethylether. Addition of petroleum ether (40°–60°) causes an oil to separate. The oil is chromatographed over silica gel (2.5g), eluting with dry ethyl acetate. The fraction containing the product (C) is concentrated under vacuum (< 30°) to about 0.5 ml. Addition of hexane, causes the product (C) to precipitate. It is removed by filtration, washed with hexane, and dried over $P_2O_5$ at 0.1 mm/25° for 3 hours to afford the product (C) as a white powder (0.09 g, 50%).

Claims to the invention follow.
What is claimed is:

1. A process for preparing compounds having the formula:

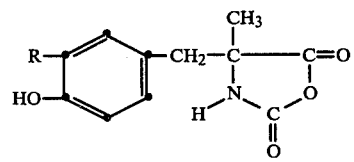

I wherein R is hydrogen or hydroxy which comprises
(A) catalytic hydrogenation in a non-aqueous system of
(a) a compound having the formula

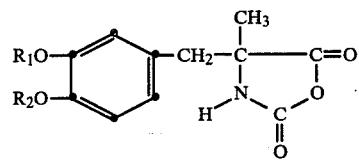

Ia wherein $R_1$ and $R_2$ are separate or joined and comprise blocking groups susceptible to removal by said hydrogenation, when R in formula I is —OH or
(b) a compound having the formula

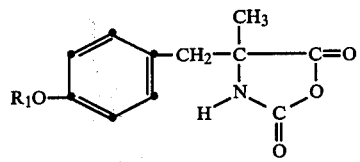

Ib wherein $R_1$ is a blocking group susceptible to removal by said hydrogenation, when R in formula I is hydrogen, or
(B) photolysis in a non-aqueous system of a compound having the formula

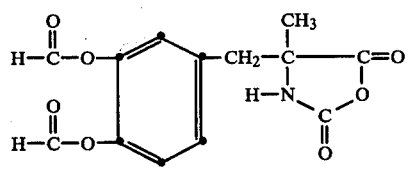

Id or

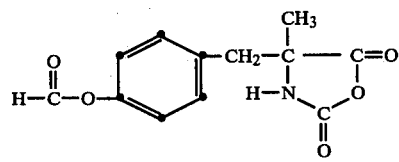

Ie

2. The process of claim 1 wherein the compounds have the S-isomer configuration.

3. The process (A) of claim 2 wherein said hydrogenation is carried out on a compound having the formula

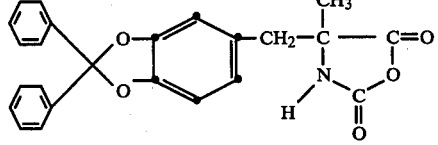

4. The process of claim 3 wherein the hydrogenation catalyst is Pd/C.

5. The process (B) of claim 1 wherein said photolysis is carried out with light of wavelength less than 400 nm.

6. The process of claim 5 wherein said photolysis is carried out in an aprotic solvent.

7. The process of claim 6 wherein said compound is Id.

8. The process of claim 7 wherein the compounds have the S-isomer configuration.

* * * * *